United States Patent [19]

van der Westhuizen et al.

[11] Patent Number: 5,330,494
[45] Date of Patent: Jul. 19, 1994

[54] KNIFE

[75] Inventors: Cornelis A. van der Westhuizen, Mein Heim, District Kimberly, Cape Province; Stephanus M. Grobler, Pretoria, both of South Africa

[73] Assignee: Cornelis A. van der Westhuizen, Cape Province, South Africa

[21] Appl. No.: 7,598

[22] Filed: Jan. 22, 1993

[51] Int. Cl.⁵ .............................. A61B 17/32
[52] U.S. Cl. ........................ 606/167; 30/2; 30/151; 30/335
[58] Field of Search ............ 606/166, 167, 170, 172; 30/2, 294, 151, 162, 164, 167, 286, 220, 335; 128/781

[56] References Cited

U.S. PATENT DOCUMENTS

| | | |
|---|---|---|
| 3,748,736 | 7/1973 | Eisen . |
| 3,905,101 | 9/1975 | Shepherd . |
| 4,086,698 | 5/1978 | Sparks ........................ 30/2 |
| 4,157,616 | 6/1979 | Lundqvist . |
| 4,393,587 | 7/1983 | Kloosterman ................ 30/162 |
| 4,531,286 | 7/1985 | Vito et al. ................... 30/2 |
| 4,980,977 | 1/1991 | Matin et al. . |

FOREIGN PATENT DOCUMENTS

| | | |
|---|---|---|
| 2108466 | 2/1971 | Fed. Rep. of Germany . |
| 1513788 | 2/1968 | France . |
| 2501097 | 9/1982 | France . |
| 70-7766 | 11/1970 | South Africa . |
| 73-3493 | 4/1973 | South Africa . |
| 87-8500 | 11/1987 | South Africa . |
| 1506572 | 4/1978 | United Kingdom . |
| 2187989 | 9/1987 | United Kingdom . |
| 2193675 | 2/1988 | United Kingdom . |
| 90-11725 | 10/1990 | World Int. Prop. O. . |

Primary Examiner—Peter A. Aschenbrenner
Assistant Examiner—William Lewis
Attorney, Agent, or Firm—Ladas & Parry

[57] ABSTRACT

A knife 10 comprises a blade holder 12, a blade 24 attached to the holder, and a protective member for the blade. Bias means 54 biasses the protective member into a first position in which protective edges 46, 48 thereof protrude beyond the blade cutting edge, so that the protective member covers the cutting edge. The protective member is movable against the biassing force exerted by the bias means, from the first position to a second position in which the cutting edge is exposed for use. First locking means locking the protective member in its first position, are also provided. The first locking means are adapted to release automatically the protective member on the protective edge of the protective member being placed against a surface to be cut and force being exerted on the blade in the direction of said surface.

10 Claims, 3 Drawing Sheets

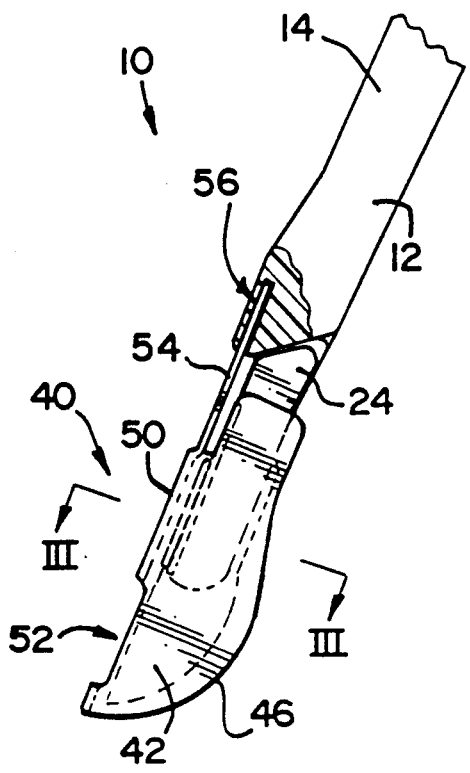
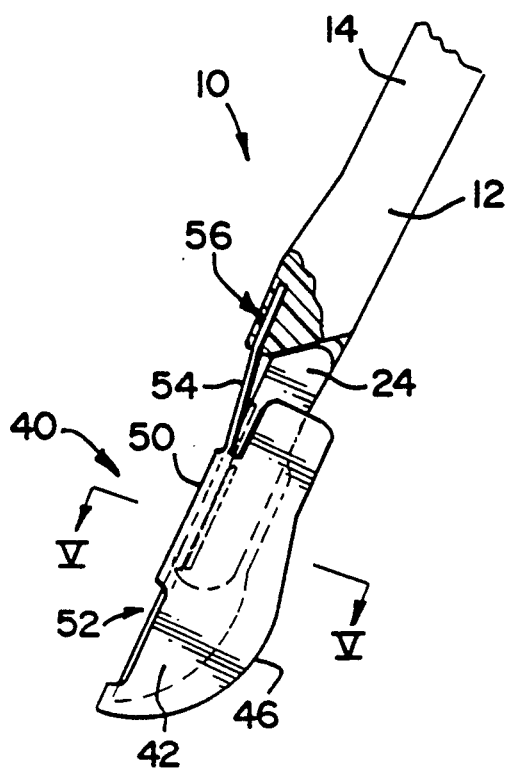
FIG 2
FIG 4
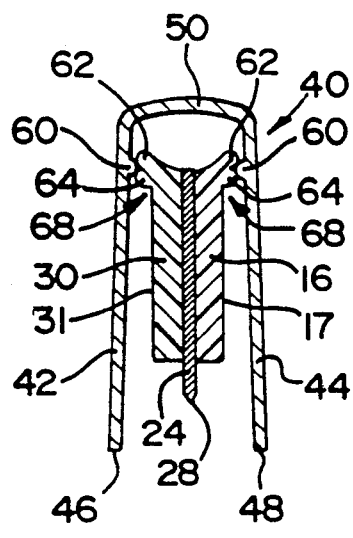
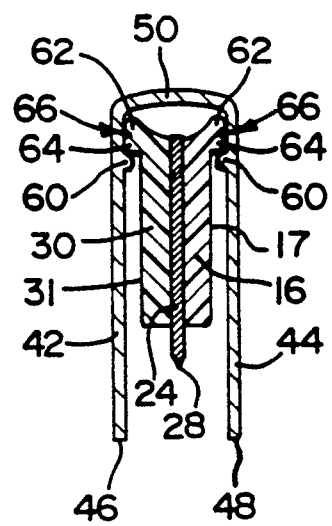
FIG 3
FIG 5

KNIFE

This invention relates to a knife. More particularly, it relates to a scalpel.

According to the invention, there is provided a knife which comprises a blade holder;

a blade, having a cutting edge, attached to the holder;

a protective member for the blade;

bias means biassing the protective member into a first position in which a protective edge of the protective member protrudes beyond the cutting edge of the blade, so that the protective member covers the cutting edge of the blade, with the protective member being movable against the biassing force exerted by the bias means, from the first position to a second position in which the cutting edge is exposed for use; and first locking means locking the protective member in its first position, the first locking means being adapted to release automatically the protective member on the protective edge of the protective member being placed against a surface to be cut and force being exerted on the blade in the direction of said surface.

The holder may be of elongate form, with the blade protruding from a first end thereof and having a single cutting edge. The blade may be fixedly attached, at the first end of the holder, to a blade attachment component forming part of the holder, and may be in the form of a scalpel blade, so that the knife is in the form of a scalpel.

The blade may be apertured, and may be sandwiched between the blade attachment component and a mounting component secured to the blade attachment component by means of at least one connecting element extending between the mounting component and the blade attachment component as well as through the blade aperture. The connecting element may protrude from the blade attachment component or from the mounting component, and be secured frictionally in an aperture in the other of the mounting component or the blade attachment component. The blade aperture may be of elongate form, and a plurality of the connecting elements may be provided. At least one of the connecting elements may protrude from the blade attachment component and be held frictionally in an aperture in the mounting component, with at least one of the connecting elements protruding from the mounting component and being held frictionally in an aperture in the blade attachment component.

The first locking means may comprise a primary locking component on the protective member and a complementary secondary locking component, with which the primary locking component engages to lock the protective member in said first position, on the blade attachment means and/or the mounting component.

The protective member may comprise a pair of protective panels located respectively on opposite sides of the blade, with each panel having said protective edge, and the panels being joined by a bridging component remote from the protective edges.

The primary locking component may comprise a protruding member on the inside of each of the panels, with the secondary locking component comprising a complementary primary recess in each of the blade attachment component and the mounting component and which hold the protruding members, thereby to lock the protective member in said first position, with the panels, protruding members and primary recesses being arranged such that the protruding members are released from the primary recesses on said force being exerted on the blade. The panels may thus be capable of flexing slightly relative to each other on said force being exerted on the blade, to permit disengagement or release of the protruding members from the primary recesses. Instead, or additionally, the protruding members and primary recesses may be suitably shaped, e.g. rounded, to permit said disengagement. The protruding members may be in the form of ridges, while the primary recesses may be in the form of troughs. Each trough may be defined between elongate raised portions of the blade attachment component, and the mounting component. When the ridge is straight, these raised portions will thus extend parallel to each other, and may be rounded to permit or facilitate said disengagement of the ridges from the troughs.

The knife may include second locking means for locking the protective member in a third position, similar to the first position and in which the protective member thus also covers the cutting edge of the blade, in such fashion that said force exerted on the blade in the direction of said surface, is insufficient to release the second locking means.

The second locking means may comprise secondary recesses in the blade attachment component and the mounting component, the secondary recesses being located closer to the blade cutting edge than the primary recesses and being arranged such that the protruding members are held more securely therein than in the primary recesses. Thus, the secondary recesses may be deeper than the primary recesses, so as to hold the ridges more securely and may be more angular, i.e. less rounded, than the primary recesses.

The panels may be transparent to facilitate viewing of the cutting edge. Instead, or additionally, at least one gap may be provided in the bridging portion to facilitate viewing of the blade.

The bias means may be in the form of a leaf spring connecting the protective member to the holder. Thus, the protective member is connected to the holder only by means of the leaf spring when the protective member is in its second position, while, when it is in its first position, it is also held to the holder by the first locking means. The protective member is thus not attached to the blade. The leaf spring may extend from the bridging portion of the protective member to the holder. The leaf spring may be integral with the bridging portion, and may be held frictionally in a passageway in the holder.

The invention will now be described by way of example with reference to the accompanying diagrammatic drawings.

In the drawings,

FIG. 2 shows, in part section, a side view of part of the knife of FIG. 1, with the protective member thereof in a first position;

FIG. 3 shows a sectional view through III—III in FIG. 2;

FIG. 4 shows, in part section, a side view similar to FIG. 2, of the knife of FIG. 1, with the protective member in a third position;

FIG. 5 shows a sectional view through V—V in FIG. 4;

Figure 1:
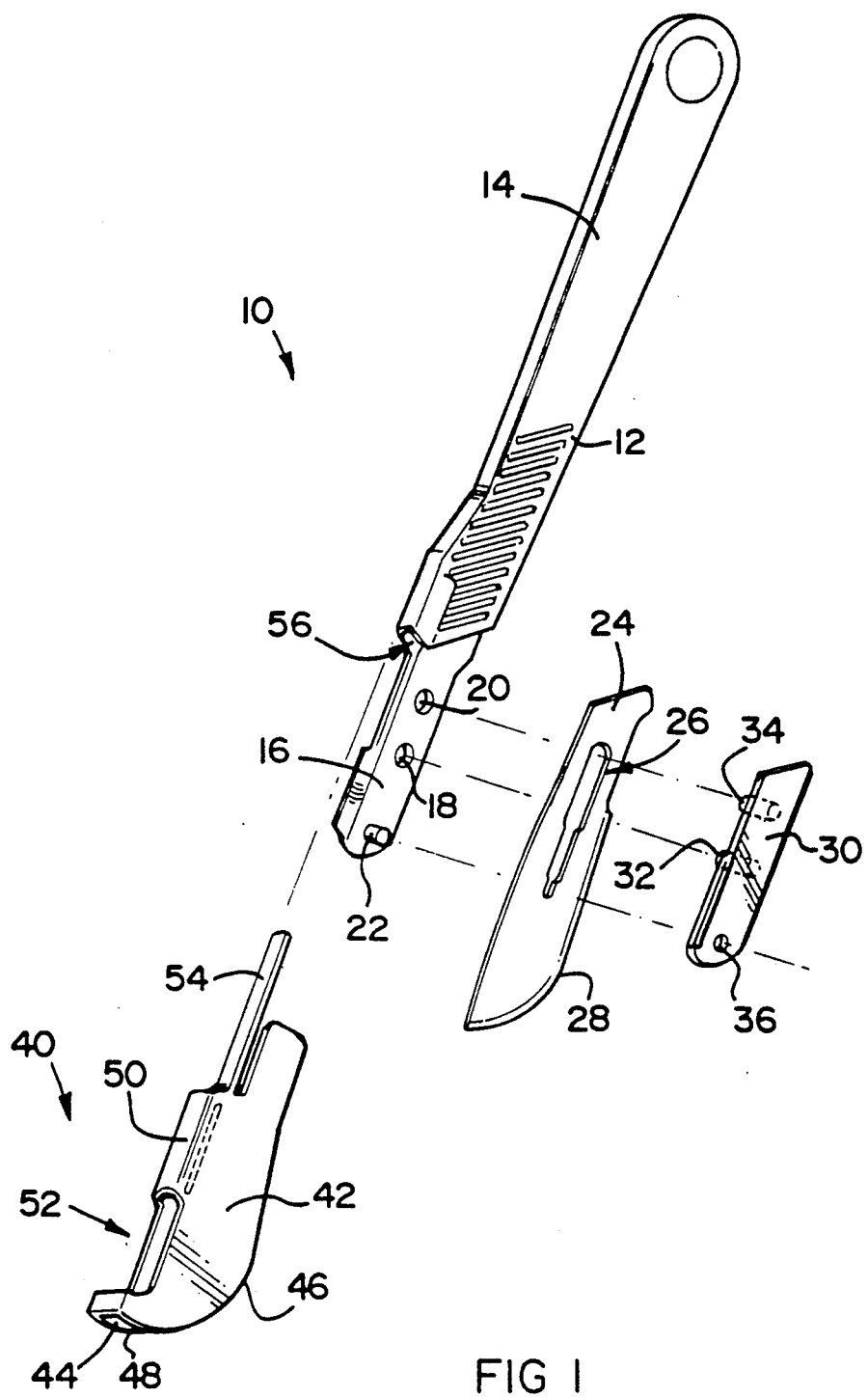
FIG. 1 shows an exploded three dimensional view of a knife in accordance with the invention.
Figure 6:
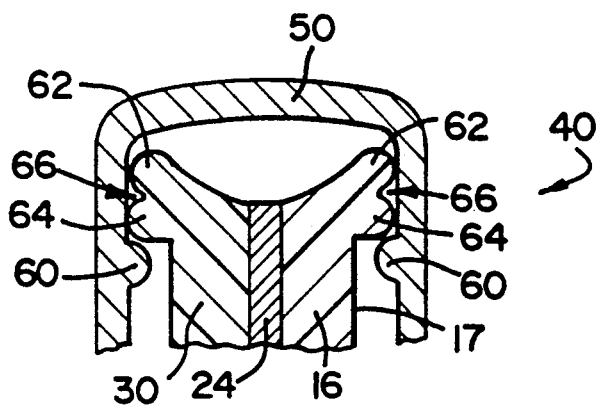
FIG. 6 shows an enlarged sectional view of part of FIG. 5.

In the drawings, reference numeral 10 generally indicates a knife, in accordance with the invention. The knife 10 is in the form of a scalpel.

The scalpel 10 includes an elongate blade holder 12 having a hand grip portion 14, and a blade attachment component 16 at one end thereof. The component 16 is somewhat thinner than the hand grip portion 14. A pair of apertures 18, 20 are provided in the component 16, while a pin 22 protrudes from it.

The scalpel 10 also includes a scalpel or surgical blade 24 having an elongate opening 26 therein. The blade 24 has a cutting edge 28.

The scalpel 10 also includes a mounting component 30. The mounting component 30 has a pair of pins 32, 34 protruding therefrom, and also has an aperture 36.

The blade 24 is sandwiched between the blade attachment component 16 and the mounting component 30, with the pins 22, 32, 34 extending through the blade opening 26 and frictionally engaging the recesses 36, 18, 20 respectively, thereby to mount the blade 24 firmly to the holder 12.

The knife 10 also includes a protective member or guard, generally indicated by reference numeral 40. The protective member 40 comprises a pair of spaced panels 42, 44 each having a protective edge 46, 48 respectively. The panels 42, 44 are connected by means of a bridging portion 50, with a gap 52 being provided in the bridging portion 50. The panels 42, 44 are transparent, and they can flex slightly relative to each other.

A leaf spring 54 protrudes from the bridging portion 50 and is received frictionally in a passageway 56 in the holder 12 so that the leaf spring 54 serves to connect the protective member 40 to the holder 12. The holder 12 is typically formed integrally of plastics material, while the leaf spring 54 can be formed integrally with the protective member 40. This combination can also be of plastics material, and can be moulded integrally.

On the inner surface of each of the panels 42, 44 is provided a straight rounded protruding ridge 60. The ridges 60 are typically moulded integrally with the panels 42, 44. On each of the components 16, 30 are provided elongate raised portions 62, 64 extending parallel to each other and defining between them a relatively shallow primary recess 66 in the form of a trough. Again, the raised portions 62, 64 are typically moulded integrally with the components 16, 30. The raised portions 62, 64 are rounded, and the significance of this will be explained in more detail hereinafter. Adjacent the raised portions 64 are defined deeper secondary recesses 68, i.e. adjacent outer surfaces 31 and 17 of the components 30 and 16 respectively. The recesses 68 are more angular than the recesses 66.

The leaf spring 54 is such that it biasses the protective member 40 to a first position, as indicated most clearly in FIGS. 2 and 3. In this position the ridges 60 engage the troughs 66, thereby holding the protective member in its first position. This will prevent accidental exposure of the cutting edge 28 of the blade 24, thereby minimizing accidental cutting or nicking.

However, when it is desired to use the scalpel 10, the protective edges 46, 48 of the panels 42, 44 respectively are placed against skin 70 to be cut with the blade 24.

On force being exerted on the blade 24, i.e. by urging the holder 12 towards the skin 70, the ridges 60 will disengage from the recesses 66. In other words, the protective member 40 is released or unlocked automatically from its first position, with no manual unlocking or triggering action being required by the user. This facilitates use of the scalpel 10.

Figures 7, 8:
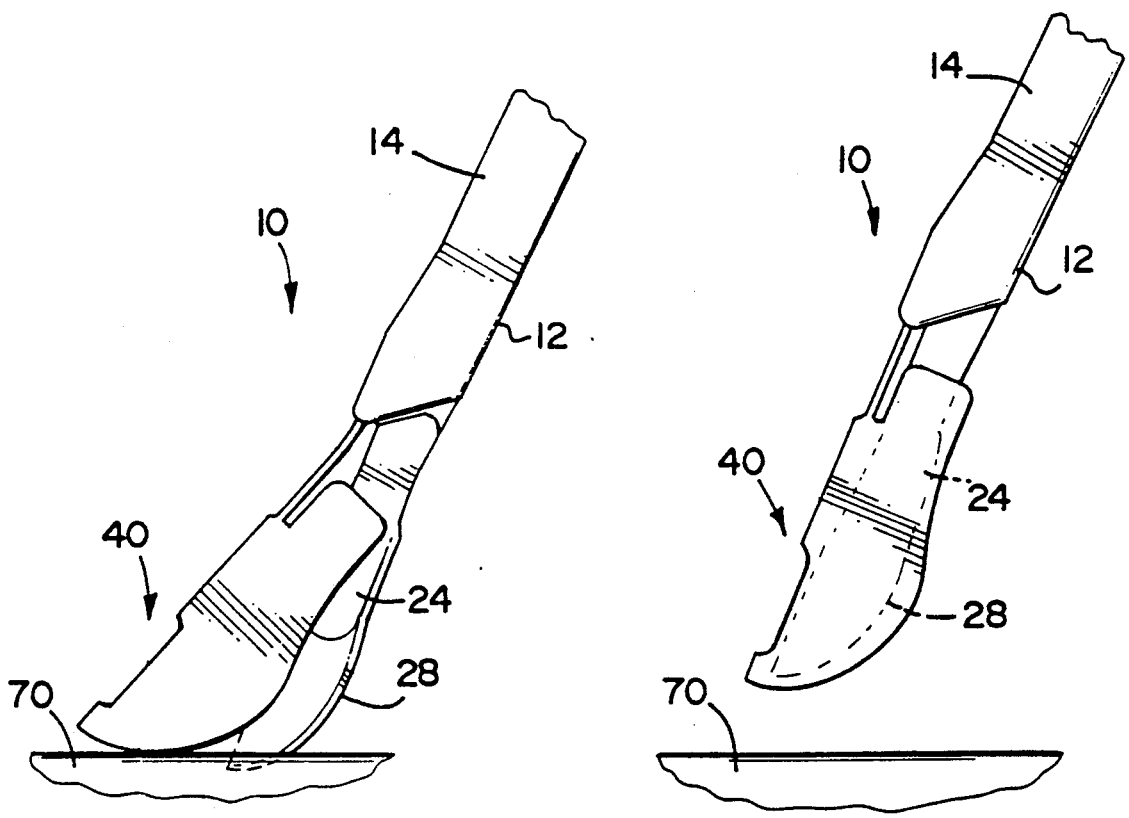
FIG. 7 shows a side view of the knife of FIG. 1, in use, with the protective member in a second position.
FIG. 8 shows a side view similar to FIG. 7, wherein the protective member has returned to its first position after use of the knife.

The protective member 40 then automatically moves or is displaced, against the bias of the spring 54, to a second position as indicated most clearly in FIG. 7, thereby exposing the cutting edge 28, and permitting the skin 70 to be cut. Accurate cutting is possible by virtue of the gap 52 in the bridging portion 50 of the protective member 40 which permits the blade to be viewed, as well as the transparent nature of the panels 42, 44.

On application of downward force on the blade being ceased, e.g. on the blade 24 being lifted clear of the skin 70, the bias of the spring 54 will urge the protective member 40 back into its first position in which it covers the blade 24, i.e. in which the protective edges 46, 48 of the panels 42, 44 protrude beyond the cutting edge 28 of the blade 24. However, the spring 54 does not necessarily urge the protective member 40 back into its locked position as indicated in FIG. 3. In other words, the ridges 60 may then merely be located alongside or in close proximity to the raised portions 62 so that automatic displacement of the protective member 40 is again effected on further use of the knife 10. Should the protective member 40 be urged back into its locked position as indicated in FIG. 3, it can then naturally again be released therefrom automatically as hereinbefore described, on the knife being used further.

When the scalpel 10 has been finally used, the protective member 40 can then be urged further over the blade 24 until the ridges 60 engage the recesses 68. In view thereof that the recesses 68 are deeper than the recesses 66 and are less rounded, the ridges 60 are held more securely in the recesses 68 than in the grooves 66. Thus, on application of equivalent force to that applied to dislodge the ridges 60 from the recesses 66, displacement of the ridges 60 from the recesses 68 will not be effected. The used scalpel can now safely be discarded or disposed, with the locking of the ridges 60 in the recesses 68 minimizing accidental displacement of the protective member or cover 40, and precluding re-use of the scalpel.

The Applicant believes that, with the scalpel 10 in which the scalpel blade 24 is fixed to the holder or handle 12 and having the protective member 40 with the locking means provided by the ridges 60 and recesses 66, 68, risks associated with known scalpels are eliminated or at least substantially reduced. For example, with re-usable scalpels, it is necessary to remove the scalpel blade after use, for example to re-fit a new scalpel blade to the holder. During such removal, and also while manipulating or carrying the scalpel, the user can be cut or nicked accidentally. This risk is to a large extent avoided with the scalpel 10 due to the protective member 40 and the locking means. Furthermore, the scalpel 10 will be discarded in its entirety after use, i.e. the blade is not replaced. This is of particular importance in reducing the risks of Aids or other viral infections which may occur if the user is accidentally cut with the used scalpel blade, as can easily occur when attempting to remove the blade of re-usable scalpels, or while carrying or handling such used scalpels.

Furthermore, the knife 10 is of relatively simple yet effective construction. For example, the protective member is connected to the holder by means of the leaf spring 54 only which permits the automatic displacement thereof as hereinbefore described, thus avoiding a costly, complicated and, potentially, problematic linkage mechanism. Due to its relatively simple construction, the knife or scalpel 10 can be made relatively inexpensively from plastics material, apart from the blade, so that it is disposable after use, as hereinbefore described.

We claim:

1. A scalpel which comprises
   an elongate blade holder having a blade attachment component at a first end thereof;
   an apertured scalpel blade having a cutting edge;
   a mounting component, with the blade sandwiched between the mounting component and the blade attachment component, and with the mounting component secured to the blade attachment component by means of at least one connecting element extending between the mounting component and the blade attachment component as well as through the blade aperture;
   a protective member for the blade and comprising a pair of protective panels located respectively on opposite sides of the blade, with each panel having a protective edge, and the panels being joined by a bridging component remote from the protective edges;
   bias means biassing the protective member into a first position in which its protective edges protrude beyond the cutting edge of the blade, so that the protective member covers the cutting edge of the blade, with the protective member being movable against the biassing force exerted by the bias means, from the first position to a second position in which the cutting edge is exposed for use;
   a primary locking component on the protective member and comprising a protruding member on the inside of each of the protective panels; and
   a secondary locking component comprising a complementary primary recess in each of the blade attachment component and the mounting component, and which hold the protruding members, thereby to lock the protective member in its first position, with the panels, protruding members and primary recesses being arranged such that the protruding members are released automatically from the primary recesses when the protective edges of the protective member are placed against the surface to be cut and force is exerted on the blade in the direction of said surface.

2. A scalpel according to claim 1, wherein the connecting element protrudes from the blade attachment component or from the mounting component, and is secured frictionally in an aperture in the other of the mounting component or the blade attachment component.

3. A scalpel according to claim 2, wherein the blade aperture is of elongate form, with a plurality of the connecting elements being provided, at least one of the connecting elements protruding from the blade attachment component and being held frictionally in an aperture in the mounting component, and at least one of the connecting elements protruding from the mounting component and being held frictionally in an aperture in the blade attachment component.

4. A scalpel according to claim 1, which includes locking means for locking the protective member in a third position, similar to the first position and in which the protective member thus also covers the cutting edge of the blade, in such fashion that said force exerted on the blade in the direction of said surface, is insufficient to release the locking means.

5. A scalpel according to claim 4, wherein the locking means comprises secondary recesses in the blade attachment component and the mounting component, the secondary recesses being located closer to the blade cutting edge than the primary recesses and being arranged such that the protruding members are held more securely therein than in the primary recesses.

6. A scalpel according to claim 1, wherein the panels are transparent to facilitate viewing of the cutting edge.

7. A scalpel according to claim 1, wherein there is at least one gap in the bridging component to facilitate viewing of the blade.

8. A scalpel according to claim 1, wherein the bias means is in the form of a leaf spring connecting the protective member to the holder.

9. A scalpel according to claim 8, wherein the leaf spring extends from the bridging component of the protective member to the holder.

10. A scalpel according to claim 9, wherein the leaf spring is integral with the bridging component and is held frictionally in a passageway in the holder.

* * * * *